United States Patent [19]

Dowling et al.

[11] Patent Number: 4,862,001
[45] Date of Patent: Aug. 29, 1989

[54] RADIANT ENERGY ABSORPTION STEAM QUALITY MONITORING MEANS AND METHOD

[75] Inventors: Donald J. Dowling; Jackie C. Sims, both of Houston, Tex.

[73] Assignee: Texaco Inc., White Plains, N.Y.

[21] Appl. No.: 141,448

[22] Filed: Jan. 7, 1988

[51] Int. Cl.$^4$ ............................................. G01N 21/35
[52] U.S. Cl. ..................................... 250/345; 250/343
[58] Field of Search .............. 73/29; 374/42; 250/343, 250/338.5, 345; 356/435, 436

[56] References Cited

U.S. PATENT DOCUMENTS

| | | | |
|---|---|---|---|
| 3,100,395 | 8/1963 | Morley | 374/42 |
| 3,281,597 | 10/1966 | Greenberg | 250/343 |
| 4,066,362 | 1/1978 | Carter | 356/440 |
| 4,137,462 | 1/1979 | Wyler | 250/573 |
| 4,712,006 | 12/1987 | Zemel et al. | 250/269 |

*Primary Examiner*—Carolyn E. Fields
*Attorney, Agent, or Firm*—Robert A. Kulason; James J. O'Loughlin; Ronald G. Gillespie

[57] ABSTRACT

A steam quality monitor measures the quality of steam flowing in a steam pipe. A measurement cell is connected in the steam pipe so that steam flows through the measurement cell. The cell has two windows aligned along an axis which is traverse to the flow axis of the steam. A source spatially arranged with the windows of the measurement cells provides IR energy which enters the measurement cells through one window and leaves through the other window so that the IR energy passes through the steam flowing in the measurement cell. An IR detector detects the IR energy as it leaves the measurement cell and provides a corresponding signal. The temperature of the steam flowing through the measurement cell is also sensed and a temperature signal provided. Circuitry derives the steam quality of the steam flowing in the steam pipe in accordance with the signal from the IR detector and the temperature signal.

16 Claims, 1 Drawing Sheet

RADIANT ENERGY ABSORPTION STEAM QUALITY MONITORING MEANS AND METHOD

BACKGROUND OF THE INVENTION

1. Field of the Invention

The present invention relates to monitors in general and, more particularly, to steam monitoring means and method.

2. Summary of the Invention

A steam quality monitor measures the quality of steam flowing in a steam pipe. A measurement cell is connected in the steam pipe so that steam flows through the measurement cell. The cell has two windows aligned along an axis which is traverse to the flow axis of the steam. A source spatially arranged with the windows of the measurement cells provides IR energy which enters the measurement cells through one window and leaves through the other window so that the IR energy passes through the steam flowing in the measurement cell. An IR detector detects the IR energy as it leaves the measurement cell and provides a corresponding signal. The temperature of the steam flowing through the measurement cell is also sensed and a temperature signal provided. Circuitry derives the steam quality of the steam flowing in the steam pipe in accordance with the signal from the IR detector and the temperature signal.

The objects and advantages of the invention will appear more fully hereinafter from a consideration of the detailed description which follows, taken together with the accompanying drawings, where one embodiment of the invention is illustrated by way of example. It is to be expressly understood, however, that the drawings are for illustration purposes only and are not to be construed as defining the limits of the invention.

DESCRIPTION OF THE INVENTION

Figure 1:
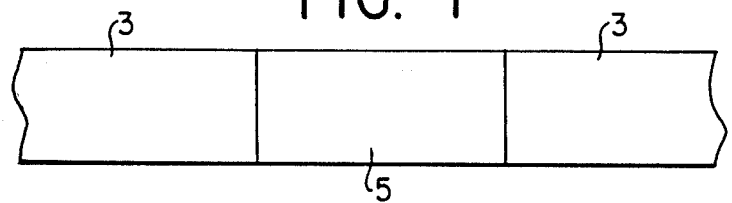
FIG. 1 is a representation of a steam pipeline with a measurement cell located therein.

The measurement of two phase gas/liquid flow has historically been a difficult and frequently inaccurate task. Conventional single phase flow measurement techniques involving the use of orifice plates, venturi tubes, etc., are usually found wanting when applied to a wide range in quality of two phase gas/liquid flow.

Accordingly a real need now exists for a means of providing inexpensive accurate real time steam quality information everywhere in a steamflood operation. Some devices have been applied to this task such as those making use of nuclear sources for measurement in the flow stream. Others obtain a side stream sample and separate it into liquid and vapor phases which are then measured separately. While there have been some successful applications of these types of devices several disadvantages can dominate the consideration of their application when viewed from the need to instrument a field containing perhaps hundreds of wells.

Nuclear sources and their protective means numbering in the tens or hundreds per field can be an expensive solution to wellhead steam quality measurement. Likewise phase separation and measurement devices would be expensive in terms of investment and maintenance due to their complexity and if configured for portable use would preclude a complete data picture in real time of the entire injection program.

Many applications of steam power through the years have made use of so-called dry steam or super-saturated steam. Both of these terms refer to steam having negligible amounts of liquid water entrained in the flow and consequently can be treated as a single phase flow of gas.

Intrumentation for monitoring single phase gas flow has been available for some time and while the technology for improving the accuracy and longevity of the instrumentation has grown the intrinsic difficulty of the measurement has not been unduly great.

Additional uses of steam where the "quality" is less than 100% ("wet steam") have grown in number, for example electric cogeneration and subterranean petroleum reservoir stimulation.

In particular, enhanced oil recovery (EOR) operations on petroleum reservoirs are increasing the applications of steam flooding of the reservoirs to increase the hydrocarbon sweep efficiency. It has been found that dry steam or super-saturated steam while transferring much heat might not provide the best overall treatment for a given field. One reason frequently given is that steam quality in the vicinity of 80% provides more immunity to pipeline scale formation and plugging. Another reason cited is the economics of today's EOR programs dictate the need for more accurate knowledge of the changing reservoir thermal characteristics. The economic considerations can also suggest revisions in the amount of steam and hot water required.

The steam quality monitor of the present invention makes an optical radiant energy absorption measurement in the steam pipeline at or near the wellhead flow control choke. The choke itself may be modified to accommodate a radiation source and a detector. The modifications should add little or no interference in the pipeline steam flow. Measurements are made at this point in the pipeline where, at the exit of the choke or orifice, the velocities of the steam gas and the water particles (together constituting the wet steam), are the same or approximately the same.

It is known that a diminution of power is suffered by a radiant beam crossing a path containing absorbent particles in proportion to the number of those absorbing particles. This knowledge can be expressed in terms of BEER's law: "Successive increments in the number of identical absorbing molecules in the path of a beam of monochromatic radiation absorbs equal fractions of the radiant energy traversing them."

Beer's law can be expressed mathematically:

(1) $A = abc$ where $A$=absorbance, $a$=absorptivity, $b$=path length, and $c$=concentration The present invention utilizes this law regarding radiation/absorption to the quantification of steam quality which goes beyond the general application of Beer's relationship. A first approximation of the fundamental concept applies even though in some ranges of steam quality and flow rate a modifying term in the mathematical expression may be required which can be determined by calibration curves or empirical means.

To apply Beer's law to steam quality, the steam quality should first be related to concentration. The concentration $C$ of a substance is the ratio of its mass to the total volume under consideration as shown in the following equation.

2. $c = m_l/v_t$
3. $V_t = V_l + V_g$
4. $V_1 = m_1 p_l$ and
5. $V_g = m_g/p_g$ where $m_g$ = mass of the gas, $m_l$ = mass of the liquid, $V_t$ = total volume, $V_l$ = liquid volume, $V_g$ = gas volume, $P_l$ = liquid density and $P_g$ = gas density.

Substituting these relationships in equation 2 above and rearranging the terms yields equation 6.

6. $c = P_l P_g/[P_g + P_l(m_g/m_l)]$

Solving equation 6 for $m_g/m_l$ and reciprocating both sides of equation 6, we arrive at equation 7.

7. $m_l/m_g = (P_l/P_g)[c/(P_l - C)]$

Steam quality, X, is generally defined as the ratio of the mass of the steam vapor or gas to the sum of the mass of the gas and the mass of the liquid water present in the wet steam and can be expressed as equation 8.

8. $X = m_g/(m_g + m_l)$

In a flowing line containing wet steam, equation 8 may be modified to take into account the slip velocity, s, which accounts for the different velocities exhibited by the gas and liquid phases. It of course would be necessary to know the values of these quantities to implement the relationship. Their determination while difficult in practice is not impossible.

By locating the measuring apparatus in or near the exit of a nozzle or orifice these difficult measurements can be avoided inasmuch as both phases can be assumed to be traveling at the same velocity at that point. Negligible measurement error is introduced by this technique.

Equation 8 may be rewritten as

9. $X = 1/(1 + m_l/m_g)$

Substituting equation 7 in equation 9 and simplifying yields equation 10.

10. $X = (c - P_l)/[(1 - P_l/P_g)c - P_l]$

From Beer's law, equation 1 is rewritten as

11. $c = A/ab$

Substituting this expression for "c" in equation 10 yields:

12. $X = (A - abP_1)/[(1 - P_1/P_g)A - abP_l]$

When a, b, $P_l$ and $P_g$ are constant for given measurement conditions then two new simplifying constants may be defined:

13. $K_1 = (1 - P_1/P_g)$ and
14. $K_2 = a b P_1$

Therefore equation 12 may be written as:

15. $X = (A - K_2)/(K_1 A - K_2)$

From this equation it can readily be seen that the steam quality, X, can be determined from the application of several geometric and instrumental constants and the measurement of the absorption of a radiant energy beam encompassing the wet steam path.

These constants in equation 15 may be obtained from handbooks, calibration procedures and standard steam line monitoring instruments.

Figure 2:
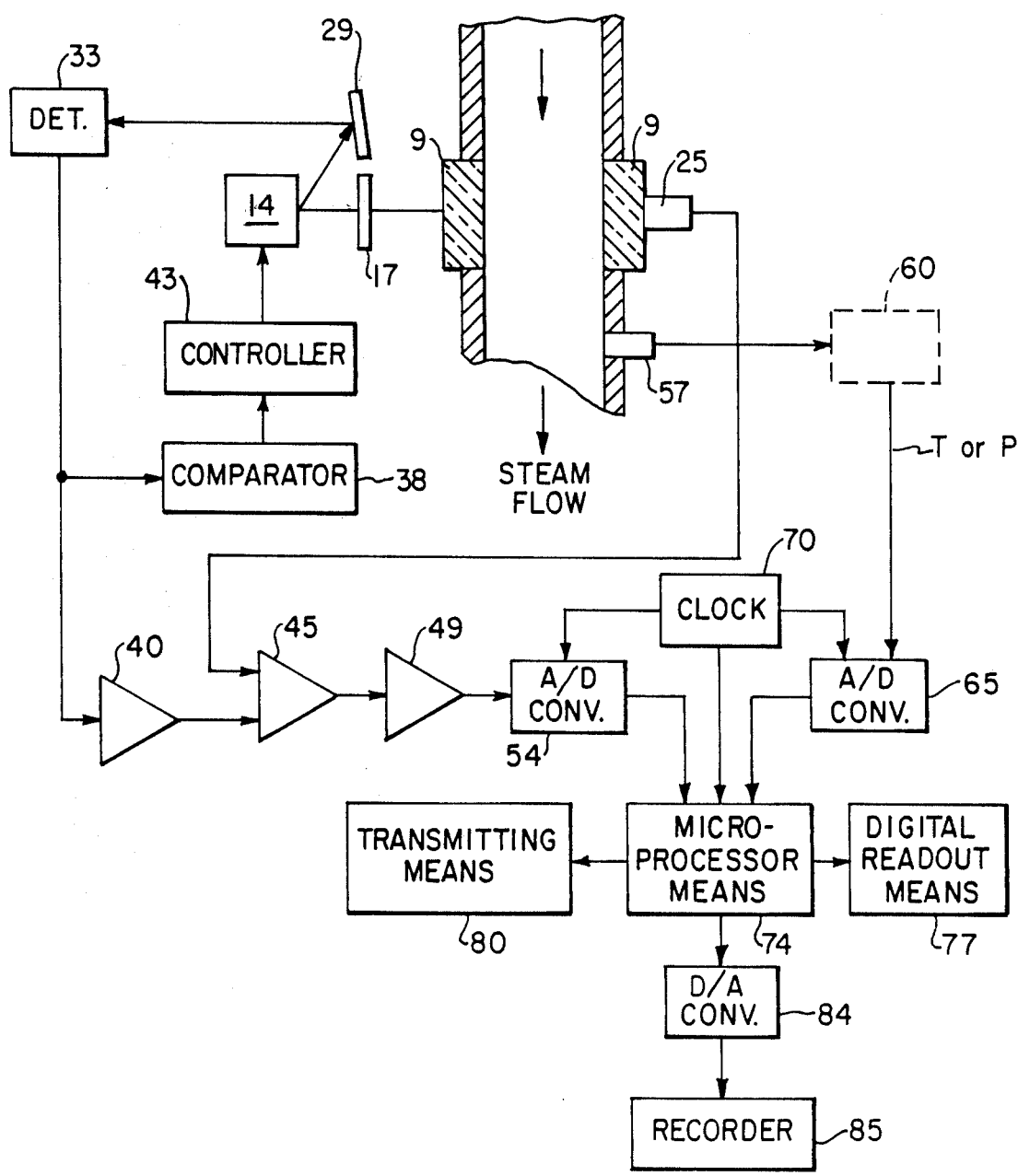
FIG. 2 is a simplified block diagram of a steam quality monitor constructed in accordance with the present invention.

However, as noted, the absorption of radiant energy must be measured. In this regard, and with reference to FIGS. 1 and 2, there is shown a pipe 3 carrying steam in which a measurement cell 5 has been interconnected so that the steam flows through measurement cell 5. Measurement cell 5 as noted previously, should be located at or near the exit of a nozzle or an orifice so that both phases can be assumed to be traveling at the same velocity. Further, measurement cell 5 has quartz windows 9 mounted therein and opposite each other so that infrared (IR) energy may enter through one window 9, cross transversely to the steam flow and exit through the other quartz window 9.

A source 14 of IR energy provides IR energy through an optical filter 17 which typically may be 3 micron filter, and passes from filter 17 through quartz window 9, traverses the steam flow and exits quartz window 9 to impinge upon an IR detector 25, which provides a signal corresponding to the IR energy impinging upon sensor 25. Source 14 also provides IR energy to a mirror 29 which reflects the energy to another IR detector 33.

Detector 33 provides a signal corresponding to the reflected IR energy impinging upon it. The signal from detector 33 is provided to a comparator 38 and to a signal conditioning amplifier 40. Comparator 38 provides a signal which is used to control a controller 43 providing an energizing voltage to source 14. Controller 43 provides the energizing voltage to source 14 in accordance with the signal from comparator 38 so as to stabilize the IR energy level provided by source 14 against aging and other variations.

Signal conditioning amplifier 40 provides a signal to a differential amplifier 45 which also receives the signal from detector 25 and provides a signal corresponding to the difference between the two signals, or in essence the difference between the source signal and the signal related to the "wet" portion of the steam as previously described. The difference signal is provided to another signal conditioning amplifier 49.

Signal conditioning amplifiers 40 and 49 serve to calibrate the response under conditions of a zero "wet" steam and maximum "wet" steam. The signal from amplifier 49 which corresponds to the wet steam is provided to analog-to-digital converter 54.

A sensor 57, which may be either a temperature sensor or a pressure sensor, senses either the temperature or the pressure of steam flowing through and provides a signal corresponding thereto. If the temperature is being sensed by use of a thermister, the thermister is connected to a sensor bridge means 60 which is shown in dash lines to indicate that if pressure is being sensed it is not necessary for the sensing of the temperature. In either case a signal T or a signal P is provided corresponding to the sensed temperature or the sensed pressure, respectively, to an analog-to-digital converter 65.

A clock 70 provides timing pulses to control the converting of the analog signals from amplifier 49 and the signal T or P by converters 54 and 65, respectively. Converters 54 and 65 provide digital signals to a microprocessor means 74 receiving timing pulses from clock 70. Microprocessor means 74 solves equation 15 and utilizes signal T or P in a conventional manner to determine the steam quality and provides the signals corresponding thereto to digital readout means 77 and to a transmitting means 80 for transmission to a central office or to a field office. Microprocessor means 74 also provides an output to a digital-to-analog converter 84 which provides a corresponding analog signal to a recorder 85.

The present invention as hereinbefore described is a steam quality monitor which uses IR energy to determine the quality of steam.

What is claimed is:

1. A steam quality monitor which measures the quality of steam flowing in a steam pipe comprising:

a measurement cell connected in the steam pipe so that steam flows through the measurement cell, said measurement cell has two windows aligned along an axis which is traverse to the flow axis of the steam, source means spatially arranged with the windows of the measurement cell for providing IR energy so as to enter the measurement cell through one window and leave through the other window so that the IR energy passes through the steam flowing in the measurement cell, first detector means arranged with the windows for detecting IR energy that has passed through the steam flow and providing a signal corresponding thereto, a mirror spatially arranged with the source means to reflect IR energy from the source means, second IR detector means spatially arranged with the mirror for detecting the reflected IR energy and providing a signal corresponding thereto, sensing means for sensing the temperature of the steam flowing through the measurement cell and providing a corresponding temperature signal, and means connected to the first and second detector means and to the sensing means for deriving the steam quality in accordance with the signals from the both detector means and the temperature signal.

2. A monitor as described in claim 1 in which the source means includes:

a source which provides IR energy, and a filter in spatial relationship between the source and the one window so as to filter the IR energy entering the measurement cell through the one window.

3. A monitor as described in claim 2 in which the deriving means includes:

a first signal conditioning amplifier means connected to the second detector means for conditioning the signal from the second detector means to provide a conditioned signal, difference amplifier means connected to the first detector means and to the first signal conditioning amplifying means for providing a difference signal corresponding to the difference between the signal from the first detector means and the conditioned signal, second signal conditioning means connected to the difference amplifier means for conditioning the signal from the difference amplifying means and providing a conditioned difference signal corresponding thereto, analog-to-digital means connected to the second signal conditioning means and to the temperature sensing means for converting the conditioned difference signal and the temperature signal to corresponding digital signals, and microprocessor means connected to the analog-to-digital converting means for determining the quality of the steam in accordance with the digital signals corresponding to the difference signal and the temperature signal, and providing an output corresponding thereto.

4. A monitor as described in claim 3 further comprising:

means connected to the second IR detector means for controlling the source in such a manner as to stabilize the IR energy being provided by the source in accordance with the signal from the second IR detector means.

5. A steam quality monitor which measures the quality of steam flowing in a steam pipe comprising:

a measurement cell connected in the steam pipe so that steam flows through the measurement cell, said measurement cell has two windows aligned along an axis which is traverse to the flow axis of the steam, source means spatially arranged with the windows of the measurement cell for providing IR energy so as to enter measurement cell through one window and leave through the other window so that the IR energy passes through the steam flowing in the measurement cell, first detector means arranged with the windows for detecting IR energy that has passed through the steam flow and providing a signal corresponding thereto, a mirror spatially arranged with the source means for reflecting IR energy, second IR detector means spatially arranged with the mirror for detecting the reflected IR energy and providing a signal corresponding thereto, sensing means for sensing the pressure of the steam flowing through the measurement cell and providing a corresponding pressure signal, and means connected to the first and the second detector means and to the sensing means for deriving the steam quality in accordance with the signals from the both detector means and the pressure signal.

6. A monitor as described in claim 5 in which the source means includes:

a source which provides IR energy, and a filter in spatial relationship between the source and the one window so as to filter the IR energy entering the measurement cell through the one window.

7. A monitor as described in claim 6 in which the deriving means includes:

a first signal conditioning amplifier means connected to the second detector means for conditioning the signal from the second detector means to provide a conditioned signal, difference amplifier means connected to the first detector means and to the first signal conditioning amplifying means for providing a difference signal corresponding to the difference between the signal from the first detector means and the conditioned signal, second signal conditioning means connected to the difference amplifier means for conditioning the signal from the difference amplifying means and providing a conditioned difference signal corresponding thereto, analog-to-digital means connected to the second signal conditioning means and to the pressure sensing means for converting the conditioned difference signal and the pressure signal to corresponding digital signals, and microprocessor means connected to the analog-to-digital converting means for determining the quality of the steam in accordance with the digital signals corresponding to the difference signal and the pressure signal, and providing an output corresponding thereto.

8. A monitor as described in claim 7 further comprising:

means connected to the second IR detector means for controlling the source in such a manner as to stabilize the IR energy being provided by the source in accordance with the signal from the second IR detector means.

9. A steam quality monitoring method for monitoring the quality of steam flowing in a steam pipe comprising the steps of:

connecting a measurement cell in the steam pipe so that steam flows through the measurement cell, said measurement cell has two windows aligned along an axis which is traverse to the flow axis of the steam, providing IR energy so as to enter the measurement cell through one window and leave through the other window so that the IR energy passes through the steam flowing in the measurement cell, detecting IR energy that has passed through the steam flow with a first IR detector, providing a first IR energy signal corresponding to the IR energy detected by the first detector, reflecting the provided IR energy with a mirror spatially arranged with a source providing the IR energy, providing a second IR energy signal corresponding to the detected reflected IR energy with a second IR detector spatially arranged with the mirror, sensing the temperature of the steam, providing a temperature signal corresponding to the sensed temperature, and deriving the steam quality in accordance with the first IR energy signal, the second IR energy signal and the temperature signal.

10. A method as described in claim 9 in which the providing the IR energy step includes:

filtering the IR energy prior to the IR energy entering the measurement cell through the one window.

11. A method as described in claim 10 in which the deriving step includes:

conditioning the signal from the second detector with a first signal conditioning amplifier to provide a conditioned signal, providing a difference signal corresponding to a difference between the conditioned signal and the first IR energy signal, conditioning the difference signal to provide a conditioned difference signal, converting the conditioned difference signal and the temperature signal to corresponding digital signals, and determining the quality of the steam in accordance with the digital signals corresponding to the difference signal and the temperature signal, and providing an output corresponding to the determined steam quality.

12. A method as described in claim 11 further comprising the step of:

controlling the source in such a manner as to stabilize the IR energy being provided by the source in accordance with the reflected IR energy signal from the second IR detector.

13. A steam quality monitoring method for monitoring the quality of steam flowing in a steam pipe comprising the steps of:

connecting a measurement cell in the steam pipe so that steam flows through the measurement cell, said measurement cell has two windows aligned along an axis which is traverse to the flow axis of the steam, providing IR energy so as to enter the measurement cell through one window and leave through the other window so that the IR energy passes through the steam flowing in the measurement cell, detecting IR energy that has passed through the steam flow with a first IR detector, providing a first IR energy signal corresponding to the IR energy detected by the first detector, reflecting IR energy with a mirror spatially arranged with a source providing the IR energy, providing a second IR energy signal corresponding to the detected reflected IR energy with a second IR detector spatially arranged with the mirror, sensing the pressure of the steam, providing a pressure signal corresponding to the sensed pressure, and deriving the steam quality in accordance with the first IR energy signal, the second IR energy signal and the pressure signal.

14. A method as described in claim 13 in which the providing the IR energy step includes:

filtering the IR energy prior to the IR energy entering the measurement cell through the one window.

15. A method as described in claim 14 in which the deriving step includes:

conditioning the signal from the second detector with a first signal conditioning amplifier to provide a conditioned signal, providing a difference signal corresponding to a difference between the conditioned signal and the first IR energy signal, conditioning the difference signal to provide a conditioned difference signal, converting the conditioned difference signal and the pressure signal to corresponding digital signals, and determining the quality of the steam in accordance with the digital signals corresponding to the difference signal and the pressure signal, and providing an output corresponding to the determined steam quality.

16. A method as described in claim 15 further comprising the step of:

controlling the source in such a manner as to stabilize the IR energy being provided by the source in accordance with the detected reflected IR energy signal from the second IR detector.

* * * * *